(12) United States Patent
Jensen et al.

(10) Patent No.: US 8,637,570 B2
(45) Date of Patent: Jan. 28, 2014

(54) PHARMACEUTICAL COMPOSITION

(75) Inventors: Klaus Jensen, Copenhagen (DK); Soren Halskov, Virum (DK); Henning Lund, Risskov (DK)

(73) Assignee: Ferring International Center S.A., St-Prex (CH)

( * ) Notice: Subject to any disclaimer, the term of this patent is extended or adjusted under 35 U.S.C. 154(b) by 450 days.

(21) Appl. No.: 12/746,052

(22) PCT Filed: Dec. 5, 2008

(86) PCT No.: PCT/IB2008/003677
§ 371 (c)(1),
(2), (4) Date: Aug. 23, 2010

(87) PCT Pub. No.: WO2009/071993
PCT Pub. Date: Jun. 11, 2009

(65) Prior Publication Data
US 2011/0015268 A1    Jan. 20, 2011

Related U.S. Application Data

(60) Provisional application No. 61/012,197, filed on Dec. 7, 2007.

(30) Foreign Application Priority Data

Dec. 7, 2007   (EP) .................................... 07254754
Jan. 8, 2008   (CN) .......................... 2008 1 0002285

(51) Int. Cl.
*A01N 37/02* (2006.01)
*A01N 37/06* (2006.01)
*A61K 31/225* (2006.01)

(52) U.S. Cl.
USPC ........... 514/547; 514/549; 514/710; 514/550; 514/529; 514/546

(58) Field of Classification Search
None
See application file for complete search history.

(56) References Cited

U.S. PATENT DOCUMENTS

| 3,211,614 A * | 10/1965 | Embring et al. ............. 514/474 |
| 6,028,065 A | 2/2000 | Ragunathan et al. |
| 2002/0146455 A1 | 10/2002 | Kundu et al. |
| 2002/0173497 A1 | 11/2002 | Ragunathan et al. |
| 2006/0004094 A1 * | 1/2006 | Agisim et al. ................ 514/537 |
| 2007/0060682 A1 | 3/2007 | Ito et al. |

FOREIGN PATENT DOCUMENTS

| BE | 708730 | 5/1968 |
| EP | 435381 A1 | 7/1991 |
| JP | 11106353 | 4/1994 |
| RU | 2189242 C1 | 9/2002 |
| WO | 0126626 | 4/2001 |
| WO | 2007002516 | 1/2007 |
| WO | 2007060682 | 5/2007 |

OTHER PUBLICATIONS

Takeichi et al. "Improvement of Aqueous Solubility and Rectal Absorption of 6-Mercaptopurine by Addition of Sodium Benzoate", Biol.Pharm.Bull., 1994, vol. 17, No. 10, pp. 1391-1394.*
Chemical Abstracts Service Registry No. 577-11-7, accessed Nov. 16, 2012.*
Chemical Abstracts Service Registry No. 99-76-3, accessed Nov. 17, 2012.*
Anonymous, "Normax Suspension or Co-danthrusate Suspension," Electronic Medicines Compendium [Online], Sep. 22, 2005.
Co-danthrusate (Normax Suspension), 2 pages (1993).
JP Office Action dated May 21, 2013, which issued in corresponding JP Application No. 2010-536545.
Package Leaflet: KLYX (in Swedish w/ English language translation), *Lakemedelsverket*, Medical Products Agency, 11 pages, (Nov. 27, 2007).
Summary of Product Characteristics: KLYX (in Swedish w/ English language translation), *Lakemedelsverket*, Medical Products Agency, 11 pages, (Nov. 27, 2007).
H.A. Krebs et al., *Studies on the Mechanism of the Antifungal Action of Benzoate*, 214 Biochem. J. 657-663 (1983).
Ananymous: "Normax Suspension or Co-danthrusate Suspension" Electronic Medicines Compendium, [online] Sep. 22, 2005, XP002477016 electronic Medicines Compendium Retrieved from the Internet: URL:http://emc.medicines.org.uk/emc/assets[retrieved on Apr. 17, 2008] the whole document.

* cited by examiner

*Primary Examiner* — James D Anderson
*Assistant Examiner* — Stephanie Springer
(74) *Attorney, Agent, or Firm* — Fish & Richardson P.C.

(57) ABSTRACT

A pharmaceutical composition comprising a docusate; an osmotic laxative; and a benzoate.

3 Claims, No Drawings

PHARMACEUTICAL COMPOSITION

CROSS REFERENCE TO PRIOR APPLICATIONS

This is a U.S. National Phase application under 35 U.S.C. §371 of International Patent Application No. PCT/IB2008/003677, filed Dec. 5, 2008, and claims the benefit of European Patent Application No. 07254754.0, filed Dec. 7, 2007; U.S. Provisional Application No. 61/012,197, filed Dec. 7, 2007; and Chinese Patent Application No. 200810002285.7, filed Jan. 8, 2008 all of which are incorporated by reference herein. The International Application published in English on Jun. 1, 2009 as WO 2009/071993 under PCT Article 21(2).

The present invention relates to pharmaceutical compositions, in particular pharmaceutical compositions for cleansing of the bowel e.g. prior to examination by proctoscopy, surgery or X-ray.

Satisfactory cleansing of the bowel is essential prior to optimal examination by proctoscopy, surgery or X-ray. Prior methods for cleansing the bowel include bowel infusion, oral administration of mixed electrolyte solution, or mannitol or sodium phosphate preparation, oral lavage solutions containing polyethylene glycol, and the use of traditional herbal medicine. There may be problems with the known methods, such as lack of efficacy, side effects and poor patient compliance.

According to the present invention there is provided a pharmaceutical composition comprising a docusate; an osmotic laxative; and a benzoate (e.g. sodium benzoate, potassium benzoate).

The composition may further comprise a $(C_1-C_6)$alkyl ester of p-hydroxybenzoic acid, for example methyl parahydroxybenzoate (methyl 4-hydroxybenzoate), ethyl parahydroxybenzoate, propyl parahydroxybenzoate or butyl parahydroxybenzoate.

Docusates are anionic surfactants. The docusate may be, for example, in the form of a salt, for example docusate sodium (sodium 1,4-bis(2-ethylhexyl)sulfosuccinate), docusate calcium (calcium 1,4-bis(2-ethylhexyl)sulfosuccinate) or docusate potassium (potassium 1,4-bis(2-ethylhexyl)sulfosuccinate). The docusate (e.g. docusate sodium) may inhibit water uptake from the human gut and reduce surface tension permitting fluid penetration of the faeces and softening of stools. The docusate (e.g. docusate sodium) may be present in an amount of between 20 to 200 mg/dose, e.g. 50 to 150 mg/dose, e.g. 110 to 130 mg/dose.

The osmotic laxative may be a sugar alcohol which has osmotic laxative effect, for example, sorbitol or lactitol. A preferred sugar alcohol for use according to the invention is sorbitol, e.g. solid sorbitol, sorbitol in aqueous solution, e.g. sorbitol 70% solution etc. Sorbitol has osmotic and lubricating properties leading to softening of the stools and facilitation of defecation. The osmotic laxative [e.g sugar alcohol which has osmotic laxative effect (e.g. sorbitol)] may be present in an amount of between 1 to 70 g/dose, e.g. 20 to 50 g/dose, e.g. 25 to 45 g/dose.

Preferably, the composition does not include a sodium phosphate salt or salts.

It has been shown that compositions according to the invention may provide rapid and effective bowel clearance (for example, compositions according to the invention may provide bowel evacuation in less than one hour).

The amount of docusate (% w/v) may be between 0.01% and 1%, e.g. between 0.05% and 0.5%, e.g. between 0.09% and 0.11%. The amount of osmotic laxative (% w/v) may be between 15% and 35% e.g. between 20% and 30%, e.g. 25%. The amount of benzoate.g. sodium benzoate, may be between 0.005% and 0.5%, e.g. between 0.01% and 0.025%, e.g. 0.018%. If present, the amount of $(C_1-C_6)$alkyl ester of p-hydroxybenzoic acid, e.g. methyl parahydroxybenzoate, may be between 0.01% and 1%, e.g. between 0.05% and 0.5%, e.g. between 0.09% and 0.11%.

The applicants have also found that the inclusion of a benzoate, e.g. sodium benzoate [e.g. together with a $(C_1-C_6)$ alkyl ester of p-hydroxybenzoic acid (e.g. methyl parahydroxybenzoate)] in a composition comprising docusate (e.g. docusate sodium) and an osmotic laxative (e.g. sorbitol) may have a remarkable effect on the stability. Compositions according to the invention have unexpectedly been shown to be stable (e.g. shown to have a change of pH value and/or composition or concentration of the docusate and/or the osmotic laxative (and other components) which is minimal— e.g. shown to have a change of pH value and/or composition or concentration of the docusate and/or the osmotic laxative (and other components) which is within shelf life limits and tolerances—e.g. shown to have a change of composition or concentration of the docusate which is less than 10%, e.g. less than 2%, e.g. less than 1%, e.g less than 0.5% and/or a change of composition or concentration of the osmotic laxative which is less than 4%, e.g. less than 2%, e.g. less than 1%, e.g less than 0.5% and/or a change of pH value which is e.g. less than 1, e.g. less than 0.7 e.g. 0.6 or less) when stored at room temperature (25° C.) for over 18 months. Further, compounds according to the invention have been shown to have minimal (e.g. less than 3% e.g. less than 2%) concentration of disodium monoctyl sulfosuccinate, the main degredation product, when stored at room temperature (25° C.) for 22 months.

The composition may be in the form of a liquid (e.g. for rectal administration). The liquid may be packaged in e.g. a single-use dose e.g. a single use container (e.g. single use bottle) with a (e.g. pre-lubricated) nozzle attached to the top of the container. The composition may be in a form suitable for administration as an enema, for example using so-called disposable bags connected to disposable tubing (despite the term disposable", such units can commonly be used for many months or years without significant deterioration); Combination Enema Syringes or "closed top" syringes; or disposable or reusable (e.g. rubber or vinyl) enema bags, bulbs or bottles. The composition may be in the form of a solution (e.g. for rectal administration).

According to the present invention in a further aspect there is provided a single use package comprising a single dose of a pharmaceutical composition comprising a docusate (e.g. docusate sodium); an osmotic laxative [e.g sugar alcohol which has osmotic laxative effect (e.g. sorbitol)]; and a benzoate (e.g. sodium benzoate). The pharmaceutical composition may further comprise a $(C_1-C_6)$alkyl ester of p-hydroxybenzoic acid, for example methyl parahydroxybenzoate. The docusate (e.g. docusate sodium) may be present in an amount (single dose) of between 20 to 200 mg, e.g. 50 to 150 mg, e.g. 110 to 130 mg. The osmotic laxative [e.g sugar alcohol which has osmotic laxative effect (e.g. sorbitol)] may be present in an amount (single dose) of between 1 to 70 g, e.g. 20 to 50 g, e.g. 25 to 40 g. The single use package may further comprise a single use container (e.g. single use bottle) with a (e.g. pre-lubricated) nozzle attached to the top of the container.

In a further aspect the present invention provides the use of a benzoate, for example sodium benzoate (for example together with methyl parahydroxybenzoate), for increasing the stability (e.g. stability at room temperature) of a pharmaceutical preparation. By "increasing the stability" it is meant that the amount of the active pharmaceutical ingredient in a preparation which includes the benzoate, and other specifications such as pH value, are less likely to change over time than those specifications in a preparation that did not include the benzoate. The preparation may be a liquid preparation, for example a liquid preparation for rectal use The preparation may include a docusate (e.g. docusate sodium) and an osmotic laxative [e.g sugar alcohol which has osmotic laxative effect (e.g. sorbitol)]. The stability may be increased such that, when the preparation is stored at room temperature (25° C.) for 18 months, there is minimal (or no) change of pH value and/or composition or concentration of the docusate and/or the osmotic laxative (and other components) in the preparation e.g. any change of pH value and/or composition or concentration of the docusate and/or the osmotic laxative (and other components) in the preparation is within shelf life limits and tolerances—e.g. any change of composition or concentration of the docusate in the preparation is less than 10%, e.g. less than 2%, e.g. less than 1%, e.g less than 0.5%; and/or any change of composition or concentration of the osmotic laxative in the preparation is less than 4%, e.g. less than 2%, e.g. less than 1%, e.g less than 0.5%; and/or any change in the pH value is e.g. less than 1, e.g. less than 0.7 e.g. is 0.6 or less.

DETAILED DESCRIPTION OF THE INVENTION

Example 1

Solution for Rectal Use

Each bottle includes:
   Docusate sodium (120 mg);
   Sorbitol (30 g);
   Sodium Benzoate (21.6 mg);
   Methyl Parahydroxybenzoate (120 mg); the balance being water.

A batch of the solution was made up by the method below and filled into special 120 ml single dose bottles for rectal use (made of low density polypropylene), as are well known in the art.

Example 2A

Stability Test

The chemical stability of the 120 ml solution of Example 1 was tested as follows.

Three batches of solutions (according to Example 1) in 120 ml sales packaging were stored for 18 months at 25° C. and 40% relative humidity (RH) (or equivalent) and tested at time points of 0 months, 3 months, 6 months, 9 months, 12 months and 18 months.

The solutions were tested for appearance, pH, density, sorbitol content (by refractive index assay), sodium docusate content (by titration method), methyl parahydroxybenzoate content (by UV assay), water loss and microbiological contamination at each time point. The methods of testing are well known in the art.

There were no significant changes in appearance and density over the test duration, which was acceptable. The pH decreased from 6.0 to between 5.4 and 5.6; in other words, after eighteen months of storage, pH is well within shelf life limits. The sorbitol assay indicated that there was an increase of about 0.7% under long term storage conditions. This is due to loss of water and is within acceptable limits (within ±4% of original weight % sorbitol). The sodium docusate assay showed acceptable increases, (within ±10% original % w/v docusate), again due to water loss, over 18 months.

The content of methyl parahydroxybenzoate decreases with increasing storage time and temperature. At 25° C. and 40% relative humidity the content is 0.98 mg/ml, well within shelf life limits (i.e. ±10% of original % w/v) after 18 months of storage.

5 bottles were checked for water loss, which was found to be about 1.2% at 25° C./40% RH after 18 months storage, due to water penetration out of the low density polyethylene container. This is within the acceptable loss of ≤5%.

There were no significant changes in the microbial limit.

Thus, the stability test on three batches of the rectal solution stabilised with sodium benzoate indicate that the product is stable for up to 18 months at 25° C./40% relative humidity.

Example 2B

Stability Test

A HPLC method was developed for the analysis of the impurities and degradation products of Docusate sodium. The main degradation product is Disodium Monoctyl Sulfosuccinate and a concentration of this product of about 1.7% was measured in samples according to the invention stored at 25° C. for 22 months. This is within acceptable limits. Thus, remarkably, compositions according to the invention are room temperature stable for 22 months or more.

Example 3

Method of Production

A sorbitol solution, a docusate sodium solution, sodium benzoate and methyl parahydroxybenzoate are stirred at room temperature until all materials are completely dissolved. The solution is filtered prior to filling and packaging. The solution is filled into special bottles (which are known in the art) for rectal use, and the bottles capped, using a fill-seal machine. The product solution is a solution suitable for rectal administration which displays remarkable stability at room temperature as described above.

The invention claimed is:

1. A pharmaceutical composition comprising:
   sodium docusate in an amount of about 0.1% w/v;
   sorbitol in an amount of about 25% w/v;
   sodium benzoate in an amount of about 0.018% w/v; and
   methyl parahydroxybenzoate in an amount of about 0.1% w/v,
   wherein said pharmaceutical composition is in the form of a solution.

2. A pharmaceutical composition according to claim 1, which has a pH of between about 5.4 and about 6.0.

3. A pharmaceutical composition according to claim 2, which maintains the pH of between about 5.4 and about 6.0 over a period of about 18 months.

* * * * *

UNITED STATES PATENT AND TRADEMARK OFFICE
CERTIFICATE OF CORRECTION

| | | |
|---|---|---|
| PATENT NO. | : 8,637,570 B2 | Page 1 of 1 |
| APPLICATION NO. | : 12/746052 | |
| DATED | : January 28, 2014 | |
| INVENTOR(S) | : Jensen et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 595 days.

Signed and Sealed this
Second Day of June, 2015

Michelle K. Lee
*Director of the United States Patent and Trademark Office*